United States Patent [19]
Sirokman et al.

[11] Patent Number: 6,047,213
[45] Date of Patent: Apr. 4, 2000

[54] ATRIAL TRACKING CARDIAC STIMULATOR

[75] Inventors: William A. Sirokman, Kirkland; Clifton A. Alferness, Redmond; John M. Adams, Issaquah, all of Wash.

[73] Assignee: Cardiac Pacemakers, Inc., St. Paul, Minn.

[21] Appl. No.: 09/034,542

[22] Filed: Mar. 3, 1998

[51] Int. Cl.[7] .......................... A61N 1/362; A61N 1/368
[52] U.S. Cl. ................................ 607/9; 607/14
[58] Field of Search ............................ 607/9, 14

[56] References Cited

U.S. PATENT DOCUMENTS

| | | | |
|---|---|---|---|
| 5,301,669 | 4/1994 | Duncan | 607/9 |
| 5,507,783 | 4/1996 | Buchanan . | |
| 5,609,610 | 3/1997 | Nappholz | 607/9 |
| 5,713,928 | 2/1998 | Bonnet et al. . | |

*Primary Examiner*—Kennedy J. Schaetzle
*Assistant Examiner*—Carl H. Layno
*Attorney, Agent, or Firm*—Foley & Lardner

[57] ABSTRACT

A atrial tracking cardiac stimulator for detecting atrial activations of a heart through an atrial lead associated with at least one of the atria of the heart and delivering ventricular pacing pulses to the heart through a ventricular lead associated with at least one of the ventricles of heart. The stimulator includes a pulse generator including an output stage which delivers a pacing pulse to the ventricular lead responsive to a conducted atrial activation. A sensor is coupled to the atrial lead for detecting atrial activations. A rejectory processor times rejectory time periods responsive to detected atrial activations. The refectory processor further provides a conducted atrial activation to the pulse generator when a detected atrial activation occurs outside of a rejectory time period.

12 Claims, 3 Drawing Sheets

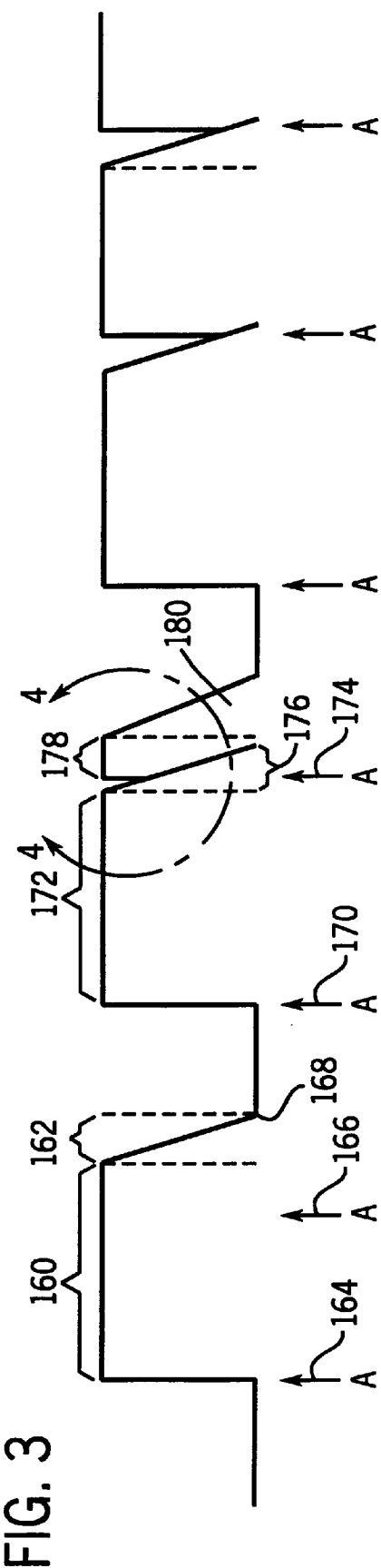
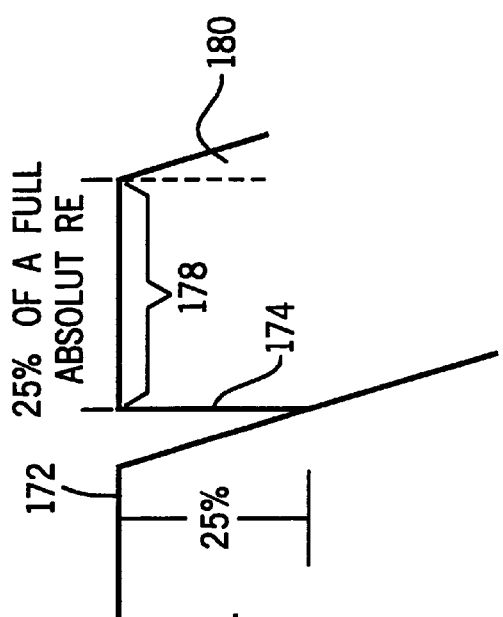

ATRIAL TRACKING CARDIAC STIMULATOR

BACKGROUND OF THE INVENTION

The present invention generally relates to an atrial tracking cardiac stimulator. The present invention more particularly relates to an implantable atrial tracking cardiac stimulator or pacemaker which senses atrial activity and paces the ventricles responsive to selected sensed atrial activations in order to regulate ventricular rates in the presence of high or increasing atrial rates. The ventricular rate regulation is seamless without requiring pacing modality modification.

Implantable pacemakers are well known in the art. Early pacemakers were single chamber pacemakers which only paced the ventricles in a trigger mode. They did not sense any cardiac activity and paced the ventricles at a predetermined, fixed rate.

Later single chamber pacemakers both sensed ventricular activity and paced the ventricles. The ventricular sensing allowed the pacemaker to inhibit pacing when a spontaneous ventricular activation (R wave) was sensed within an escape interval corresponding to the fixed pacing rate. Such pacing is referred to as demand pacing since the heart is paced only when necessary. This pacing modality is referred to in the art as VVI pacing.

As the pacemaker art advanced, dual chamber pacemakers were made available. The first dual chamber pacemakers sensed in both the atria and ventricles and paced the ventricles. These dual chamber pacemakers were primarily for heart block patients who suffered from lack of conduction between the atria and ventricles. Their purpose was to simulate normal atrial-ventricular synchrony in heart block patients by coupling ventricular response to atrial activity. When an atrial activation (P wave) was sensed, it started the timing of an AV delay. At the end of the AV delay, the ventricles were paced. The most significant benefit of the foregoing was that when the atrial rate increased due to exercise or some other cause of increased metabolic demand, the ventricular rate would similarly increase so that the hemodynamic output of the heart would satisfy the metabolic demand. Such pacemakers could also function in a demand mode supported by ventricular sensing.

Atrial pacing was later added to the capabilities of dual chamber pacemakers. These pacemakers are referred to in the art as DDD pacemakers. They not only assist heart block patients by coupling the atria and ventricles, but further promote atrial function in sick-sinus syndrome patients whose atria generally do not function properly on their own.

While current dual chamber pacemakers have done much to treat cardiac patients, and especially those with sick-sinus syndrome and heart block, such devices are not without their problems. For example, when a heart block patient experiences a rapid atrial rate, a dual chamber pacemaker will pace the ventricles at the high atrial rate due to the coupling between the atria and the ventricles. If the high atrial rate is not due to metabolic demand, but instead due to an atrial tachyarrhythmia, such as atrial flutter or atrial fibrillation, the ventricular rate will be higher than required to meet metabolic demand. In a sense, the pacemaker would drive the heart too fast for these conditions.

To overcome the above problems associated with DDD pacing and the presence of atrial tachyarrhythmias, mode switching was added to these devices. The mode switching would cause the pacemaker to switch from a DDD mode to a VVI mode set to pace at an essentially normal rate. An abrupt change in ventricular rate can occur at the point of the mode switch which many patients find objectionable. One such DDD pacemaker is described in U.S. Pat. No. 4,624,260 which mode switches from the DDD modality to the VVI modality in response to high atrial rates.

Another problem with DDD pacemakers is that by their very nature, together with the human physiology of the heart, the pacemaker can cause a fast rate on its own. This condition is known as a pacemaker mediated tachycardia (PMT) and occurs when the pacemaker senses a P wave which resulted from a paced or spontaneous ventricular activation retrogradedly conducted to the atrium. As a result, the retrogradedly conducted R wave is sensed as a P wave and initiates a device AV pacing delay. At the end of the AV delay, the ventricle is paced to set up another retrogradedly conducted R wave. If this is allowed to persist, a very fast heart rate can result. To preclude and/or terminate a PMT, dual chamber pacemakers incorporate additional PMT prevention and/or termination functionality.

The present invention represents a further improvement in the evolution of the dual chamber pacemaker. It tracks the atrial rate. However, through a unique rejectory processor, it paces the ventricles after an AV interval for only selected ones of the detected P waves for regulating the ventricular rate in the presence of a high atrial rate. It accomplishes this end seamlessly without requiring mode switching. Further, pacemaker mediated tachyarrhythmias are automatically precluded thus rendering additional PMT prevention and/or termination functionality unnecessary.

SUMMARY OF THE INVENTION

The invention provides an atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart. The stimulator includes a pulse generator including an output stage for delivering a pacing pulse to the ventricles, a sensor coupled to the atrial lead for detecting atrial activations, and means for timing rejectory time periods responsive to detected atrial activations and causing the pulse generator output stage to deliver a pacing pulse responsive to a detected atrial activation occurring outside of a rejectory time period.

The invention further provides an atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart. The stimulator includes a pulse generator including an output stage for delivering a pacing pulse to the ventricular lead responsive to a conducted atrial activation and a sensor coupled to the atrial lead for detecting atrial activations. The stimulator further includes a rejectory processor for timing rejection time periods responsive to detected atrial activations and providing a conducted atrial activation responsive to a detected atrial activation occurring outside of a rejectory time period.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements and wherein;

FIG. 3 is a diagram of additional timing signals which may occur in the cardiac stimulator of the present invention in accordance with a secondary embodiment thereof; and FIG. 4 is a partial exploded view, to an enlarged scale, of a timing signal of FIG. 3.

DETAILED DESCRIPTION OF THE PREFERRED EMBODIMENT

Figure 1:
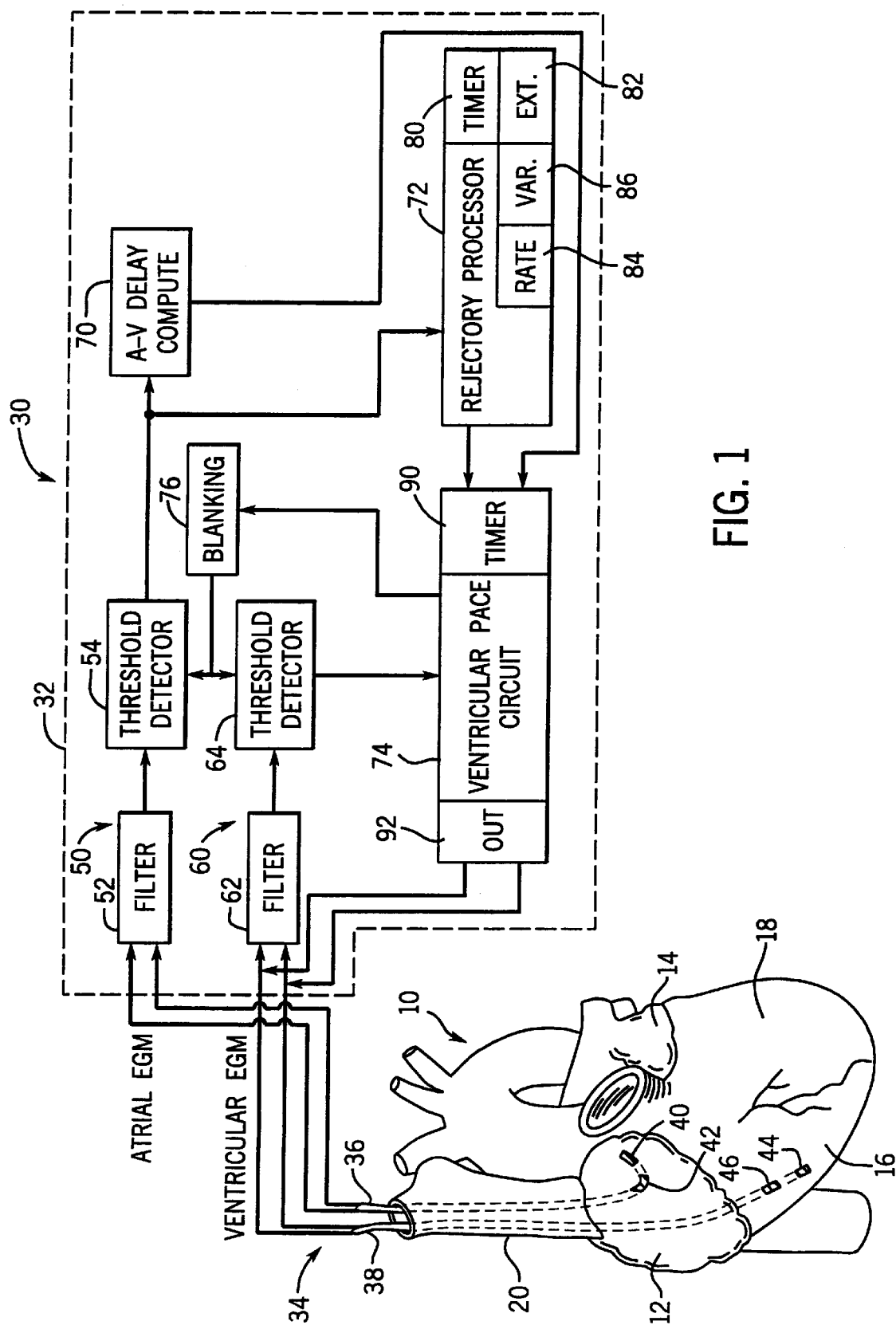
FIG. 1 is schematic block diagram of a fully implantable atrial tracking cardiac stimulator embodying the present invention shown in association with a human heart in need of pacing management.

Referring now to FIG. 1, it illustrates a fully implantable atrial tracking cardiac stimulator 30 embodying the present invention shown in association with a human heart 10 in need of pacing management. The portions of the heart 10 illustrated in FIG. 1 and which are relevant to the understanding of the present invention are the right atrium 12, the left atrium 14, the right ventricle 16, the left ventricle 18, and the superior vena cava 20. The cardiac stimulator 30 generally includes an enclosure 32 and a lead system 34 including a first endocardial lead 36 and second endocardial lead 38. The first endocardial lead 36 is associated with the right atrium 12 of the heart 10 and includes a bipolar electrode pair including a distal or tip electrode 40 and a proximal electrode 42. The electrodes 40 and 42 are arranged to be in contact with an inner wall of the right atrium 12 to permit sensing of atrial activity. If atrial pacing is also to be employed, the electrodes 40 and 42 may also be utilized for applying pacing stimuli to the atria as well. The second endocardial lead 38 is associated with the right ventricle of the heart and includes a further bipolar electrode pair including a distal or tip electrode 44 and a proximal electrode 46. The electrodes 44 and 46 are arranged to make electrical contact with an inner wall of the right ventricle 16 to permit both the sensing of ventricular activity within the right ventricle and the application of pacing pulses to the right ventricle.

Within the enclosure 32 the cardiac stimulator 30 includes an atrial channel 50 including a bandpass filter 52 and a threshold detector 54 and a ventricular channel 60 including a bandpass filter 62 and threshold detector 64. The cardiac stimulator 30 further includes an AV delay processor 70, a rejectory processor 72, a ventricular pacing circuit 74, and a blanking circuit 76. The rejectory processor includes a timer 80, a refectory time period extender 82, an atrial rate determining stage 84, and an atrial rate variability determining stage 86. Lastly, the ventricular pacing circuit 74 includes a timer 90 and an output stage 92.

The electrodes 40 and 42 of the right atrial lead 36 are coupled to the bandpass filter 52. The output of the bandpass filter 52 is coupled to the threshold detector 54 which detects atrial activity and more particularly detects atrial activations or P waves of the atria. The output of the threshold detector 54 is coupled to an input of the AV delay processor 70 and to an input of the rejectory processor 72.

Whenever a P wave is detected by the threshold detector 54, the AV delay processor 70 computes an AV delay time period to be potentially used for pacing the ventricles at the end of the AV delay time period. In computing the AV delay time period, the AV delay processor preferably averages the atrial rate over the last eight or ten atrial intervals, for example, and determines an AV delay time period based upon that average. Generally, the AV delay time period will have a duration directly related to the average atrial interval. Hence, when the atrial rate is high, the AV delay time period will be relatively short. Conversely, when the atrial rate is low, the AV delay time period will be relatively long. As will be appreciated by those skilled in the art, the AV delay time period should be limited at both the short duration and long duration extremes to provide a minimum AV delay time period of, for example, 50 milliseconds, and a maximum AV delay time period of, for example, 150 milliseconds.

The timer 80 of the rejectory processor 72 times rejectory time periods responsive to detected atrial activations. The timer 80 begins the timing of a rejectory time period in response to a detected P wave. If a P wave is detected at a time wherein the timer 80 is not timing, and in other words has timed out, the P wave will be conducted from the refectory processor to the ventricular pacing circuit 74 as a conducted atrial activation or conducted P wave. To that end, it will be noted that the output of the rejectory processor 72 is coupled to an input of a ventricular pacing circuit 74. The duration of the rejectory time periods, as will be seen hereinafter, may vary depending upon an atrial rate determined by the atrial rate determining stage 84, the variability of the atrial rate as determined by the atrial rate variability determining stage 86, or, as will be seen hereinafter with respect to FIGS. 3 and 4, the time in which an atrial activation is detected.

As will further be noted in FIG. 1, the output of the AV delay processor 70 is coupled to an input of the ventricular pacing circuit 74. If a P wave or atrial activation is conducted to the ventricular pacing circuit 74 by the rejectory processor 72, the AV delay time period determined by the AV delay processor 70 for that conducted atrial activation or P wave is used by the timer 90 to time an AV delay time period. If a spontaneous ventricular activation is not detected before the end of the AV delay time period timed by the timer 90, the output stage 92 will provide a pacing output pulse to the ventricular lead 38 for application to the right ventricle from the electrodes 44 and 46. This will cause a paced ventricular activation of the right ventricle 16 and left ventricle 18.

Upon application of the pacing pulse to the ventricles, and for a short time thereafter, the blanking circuit 76 forces the threshold detectors 54 and 64 into a blanking mode for a blanking time period, of, for example, 100 milliseconds. The blanking of the threshold detectors 54 and 64 precludes the threshold detectors from saturating to assure a quick detection response once the blanking period has ended. It also assures that ventricular pacing pulse artifacts are not detected in the atrial channel and mistaken for detected atrial activations. The blanking time period is relatively short to assure that significant cardiac activity does not go undetected.

The right ventricular lead 38 is also coupled to the inputs of the filter 62. The filter 62 is coupled to the threshold detector 64. As a result, the threshold detector 64 detects ventricular activations or R waves of the ventricles. The output of the threshold detector is coupled to the ventricular pacing circuit 74. This permits demand pacing. If the ventricular pacing circuit is to pace the ventricles but during the AV delay time period an intrinsic or spontaneous ventricular activation or R wave is detected by the threshold detector 64, the ventricular pacing circuit will be inhibited and will not apply the pacing pulse to the ventricles.

Figure 2:
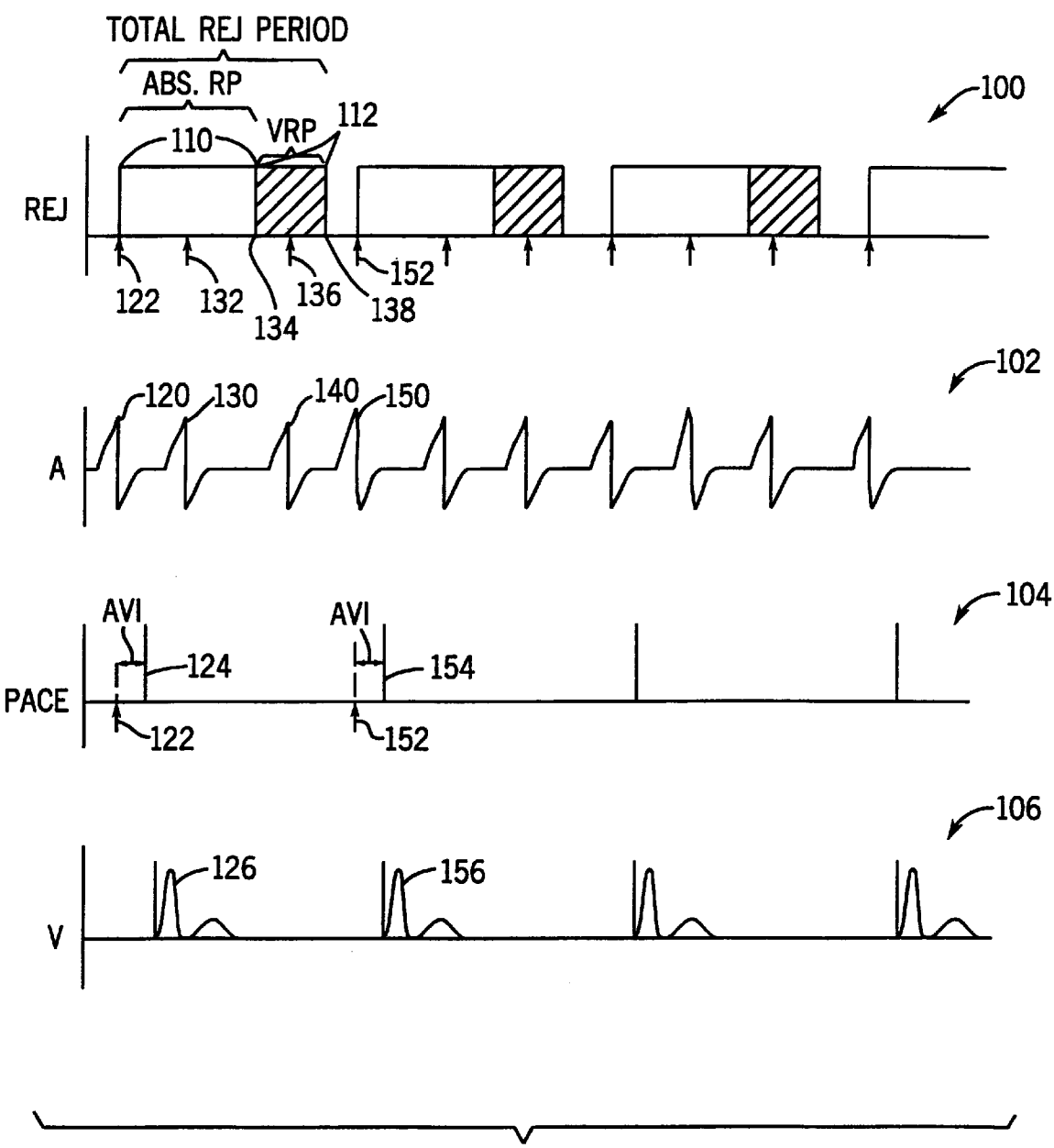
FIG. 2 is a diagram of atrial and ventricular signals and associated timing signals which occur in the cardiac stimulator of the invention.

Reference is now made to FIG. 2. The first signal waveform 100 of FIG. 2 illustrates the condition of the timer 80 of the rejectory processor 72. The second signal waveform 102 illustrates the atrial electrogram as seen at the input of the threshold detector 54. The third signal waveform 104 illustrates the output of the ventricular pacing circuit 74 and the timing of the AV delay time interval by the timer 90. Lastly, the fourth signal waveform 106 illustrates the ventricular electrogram as seen across the inputs of the filter 62.

In accordance with this first preferred embodiment of the present invention, the rejectory processor timer 80 times a base or absolute refectory time period 110 and under high atrial rate or high atrial rate variability conditions a variable refectory time period 112 immediately after the base refectory time period 110. The base rejectory time period 110 may be, for example, 400 milliseconds. The variable refectory time period may range from 0 to 200 milliseconds, for example, so that a total rejectory time period may range between 400 and 600 milliseconds. The extent to which the base rejectory time period is extended by the variable rejectory time period may depend upon the atrial rate, for example. The extent of the refectory period extension may be linearly related to atrial rate over a relatively narrow atrial rate range. For example, for atrial rates below 150 P waves per minute the variable refectory period may be 0 milliseconds. However, for an atrial rate of 200 P waves per minute, the variable refectory period may be the full 200 milliseconds. Further, the variable refectory period duration may be linearly related to the atrial rate within the atrial rate range for determining the variable refectory period. As a result, for atrial rates of 150 P waves per minute and lower, the refectory period will be the base rejectory period of 400 milliseconds. For atrial rates of 200 P waves per minute and above, the total refectory period will be 600 milliseconds. For atrial rates between 150 and 200 P waves per minute, the total rejectory period will extend linearly from 400 milliseconds to 600 milliseconds. Again, it should be understood, that these particular ranges are offered as being exemplary only.

The atrial rate for determining the duration of the refectory period is preferably determined by the atrial rate determining stage 84. It preferably averages a last predetermined number of atrial intervals to determine the atrial rate. For example, the last eight or ten intervals may be used to determine the atrial rate.

The refectory period extending stage 82 causes the timer 80 to extend the rejectory period responsive to the atrial rate determined by the atrial rate determining stage 84. The rejectory period extending stage 82 will cause the timer 80 to extend its timing if the atrial rate is above a maximum base rejectory period rate, as previously described.

Referring now to the second signal waveform 102 of FIG. 2, as depicted therein an atrial activation or P wave 120 is detected by the threshold detector 54 at 122. Because the rejectory time period timer 80 was timed out at the time of the detection of the atrial activation 120, the detection of the atrial activation 120 begins the timing of a new rejectory time period at 122.

Coincident with the beginning of the timing of the rejectory time period, the detection of the atrial activation 120 causes the AV delay processor 70 to compute a new AV delay time interval. Also, the atrial activation 120, since it is detected outside of a rejectory time period, is conducted to the ventricular pacing circuit 74 at 122 to cause the timer 90 of the ventricular pacing circuit 74 to begin timing the AV delay time period interval. As can be seen in the third signal waveform 104, at the end of the AV delay time period interval, the pacing output stage 92 provides a pacing pulse to the ventricular lead 38 and hence electrodes 44 and 46 at time 124. This in turn causes the generation of ventricular activation 126 of the third signal waveform 106.

The next atrial activation 130 is detected at time 132. The detection of the atrial activation 130 at time 132 occurs during or within a rejectory time period being timed by the refectory time period timer 80 of the rejectory processor 72. As a result, the atrial activation 130 is not conducted from the output of the rejectory processor 72 to the ventricular pacing circuit 72 for initiating the timing of an AV delay time period. However, the atrial activation 130 still causes the AV delay processor 70 to compute an AV delay time period, and the atrial rate determining stage 84 to compute an atrial rate as previously described for potential use in association with the detected atrial activation 130.

As depicted in FIG. 2, the atrial rate is above the base refectory period atrial rate such that at time 134, when the base refectory period is timed out, tho rejectory period extending stage 82 causes the timer 80 to continue timing for the extended variable refectory period 112. During the time of the extended rejectory period, the next atrial activation 140 is detected at time 136. Since the atrial activation 140 is not detected outside of a rejectory period, it is not conducted from the output of the rejectory processor 72 to the input of the ventricular pacing circuit 74 for setting up the timing of an AV delay time period by the timer 90. However, as with the case of the atrial activation 130, the atrial activation 140 when detected causes the AV delay processor 70 to compute a new AV delay time period for potential use and the atrial rate determining stage 84 to compute a new average atrial rate.

At time 138, the total rejectory period ends. As will be noted, the timer 80 of the rejectory processor 72 has timed out.

The next atrial activation 150 is detected by the threshold detector 54 at time 152 outside of a refectory time period. As a result, at time 152, the detection of the atrial activation 150 causes the timer 80 of refectory processor 72 to begin the timing of another rejectory time period. The atrial activation 150 also upon being detected causes the AV delay processor 70 to determine a new AV delay time period. At time 138 upon detection of the atrial activation outside of a rejectory time period, the timer 90 of the ventricular pacing circuit 74 is caused to initiate the timing of an AV delay time period. At the end of the AV delay time period 154, the output stage 92 of the ventricular pacing circuit 74 applies a pacing pulse to the ventricular lead 38 and thus to electrodes 44 and 46 for pacing the ventricles at time 154 to induce a ventricular activation 156.

As will be noted from the second signal waveform 102, the atrial rate is at a substantially high rate while the ventricular rate is at a much lower rate. Hence, as can be seen from the foregoing, the atrial tracking cardiac stimulator of the present invention is capable of regulating the ventricular rate in the presence of a high atrial rate. It accomplishes this end without mode switching and by virtue of the rejectory periods which are established as previously described, the cardiac stimulator automatically precludes a sustained pacemaker mediated tachycardia.

As will also be appreciated by those skilled in the art, atrial pacing could be added to the functionality of the cardiac stimulator of FIG. 1. Such atrial pacing was omitted so as to not unduly complicate the description of the atrial tracking cardiac stimulator of the present invention.

As previously mentioned, the duration of the variable rejectory time period may be based upon atrial rate variability. To that end, the atrial rate variability stage 86 may determine a standard deviation in the rates determined by the atrial rate determining stage 84. That standard deviation may then be used to control the duration of the variable refectory time period with greater deviations causing longer durations and smaller deviations causing shorter durations.

Referring now to FIGS. 3 and 4, these Figures illustrate the manner in which the timer 80 of the refectory processor 72 may time rejectory time periods in accordance with an alternative embodiment of the present invention. This alternative embodiment is based upon the emulation of the intact atrioventricular (AV) node of the human heart which controls the coupling between the atrial and the ventricles. More specifically, as will be noted in FIG. 3, the timer 80 of the rejectory processor 72 times a base rejectory time period 160 to duplicate the time in which all of the cells of the AV node are refractory, and a relative rejectory time period to duplicate the gradual nonrefractoriness of the AV node cells. With more specific reference to FIG. 3, it will be noted that an atrial activation detected at 164 causes the timer 80 to begin timing the absolute rejectory period 160. The atrial activation 164, in addition to causing the timer 80 to time the absolute rejectory period 160, also is conducted to the ventricular pacing circuit 74 for the generation of a pacing pulse after an AV time delay computed by the AV delay processor 70.

Another atrial activation 166 occurs during the absolute rejectory period 160. It has no effect on the timing of the absolute rejectory period 160 and is not conducted to the ventricular pace circuit 74. However, the time between the atrial activation 164 and the atrial activation 166 is utilized in computing a new AV delay time period by the AV delay processor 70 and also an updated atrial rate by the atrial rate determining stage 84. As will be further noted in FIG. 3, an atrial activation is not sensed during the relative rejectory period 162 permitting the counter 80 to reset at 168.

The next atrial activation to be detected 170 causes the timer 80 to begin timing a new absolute rejectory time period 172 and to conduct the atrial activation to the ventricular pacing circuit 74 for the generation of a ventricular pacing pulse after a suitable AV delay time period calculated by the AV delay processor 70. The next atrial activation to be detected 174 occurs during the relative rejectory period 176 following the absolute refectory period 172 and hence is not conducted to the ventricular pace circuit 74. As will be noted in FIG. 4, the atrial activation sensed at 174 occurs after 25% of the relative refectory time period has been completed. As a result, the extension stage 182 causes the timer 70 to extend the rejectory period by an extension time period which is 25% of the full absolute refectory time period. This extension time period is indicated at 178 in FIGS. 1 and 4. This emulates the condition of the AV nodal cells in which they are 25% repolarized from their previously completely depolarized and absolutely refractory state. In this partially repolarized state, the cells can be electrically activated, but do not elicit a complete action potential and may not cause cell-to-cell propagation.

As will be further noted in FIGS. 3 and 4, after the extended refectory time period 178 is completed, a new relative refectory time period 180 is started by the timer 80 of the refectory processor 72.

As can be seen from the foregoing with respect to FIGS. 3 and 4, this embodiment provides an approximation of the manner in which the AV node functions in the human heart. By establishing the absolute, relative, and extended refectory time periods as described above, not every atrial activation is conducted to the ventricular pacing circuit 74 to cause the generation of a pacing pulse. As a result, even though the atrial rate may be increasing or be very fast, regulation of the ventricular rate in a manner emulating the operation of the AV node is achieved in accordance with this additional embodiment of the present invention.

While particular embodiments of the present invention have been shown and described, modifications may be made. For example, the present invention may also find applicability in rate responsive pacemakers. Additionally, as previously mentioned, atrial pacing could also have been added to the functionality of the heart stimulator shown in FIG. 1 and other sensing vectors, such as the right atrium to coronary sinus sensing vector, may be employed to detect the atrial activations without departing from the present invention. As a result, it is intended in the appended claims to cover all such changes and modifications which fall within the true spirit and scope of the present invention.

What is claimed is:

1. An atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart, the stimulator comprising:

a pulse generator including an output stage for delivering a pacing pulse to the ventricular lead;

a sensor coupled to the atrial lead for detecting atrial activations; and means for initiating timing of a rejectory time period only responsive to each detected atrial activation occurring outside of a rejectory time period and enabling the pulse generator output stage to deliver a pacing pulse responsive only to a detected atrial activation occurring outside of a rejectory time period.

2. An atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart, the stimulator comprising:

a pulse generator including an output stage for delivering a pacing pulse to the ventricular lead responsive to a conducted atrial activation;

a sensor coupled to the atrial lead for detecting atrial activations; and a rejectory processor for timing a rejectory time period responsive to each detected atrial activation occurring outside of a rejectory time period and providing a conducted atrial activation responsive only to a detected atrial activation occurring outside of a rejectory time period.

3. An atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart, the stimulator comprising:

a pulse generator including an output stage for delivering a pacing pulse to the ventricular lead responsive to a conducted atrial activation;

a sensor coupled to the atrial lead for detecting atrial activations; and a rejectory processor for timing rejectory time periods responsive to detected atrial activations and providing a conducted atrial activation responsive to a detected atrial activation occurring outside of a rejectory time period wherein the rejectory processor includes timing means for timing a rejectory time period responsive to each conducted atrial activation.

4. An atrial tracking cardiac stimulator for detecting atrial activations of a heart through an atrial lead associated with at least one of the atria of the heart and delivering ventricular pacing pulses to the heart through a ventricular lead associated with at least one of the ventricles of the heart, the stimulator comprising:

a pulse generator including an output stage for delivering a pacing pulse to the ventricular lead responsive to a conducted atrial activation;

a sensor coupled to the atrial lead for detecting atrial activations; and a rejectory processor for timing rejectory time periods responsive to detected atrial activations and providing a conducted atrial activation responsive to a detected atrial activation occurring outside of a rejectory time period wherein the rejectory processor includes timing means for timing a base rejectory time period responsive to each conducted atrial activation and extension means for causing the timing means to time rejectory time period extensions following selected base rejectory time periods.

5. A cardiac stimulator as defined in claim 4 wherein the extension means includes means for causing the timing means to time a rejectory time period extension responsive to an atrial activation being detected during a rejectory time period.

6. A cardiac stimulator as defined in claim 4 wherein the rejectory processor includes atrial rate determining means for determining a rate of the detected atrial activations and wherein the extension means causes the timing means to time a rejectory time period extension responsive to the atrial rate.

7. A cardiac stimulator as defined in claim 4 wherein the refectory processor includes atrial rate variability determining means for determining a variability in detected atrial activation rate and wherein the extension means causes the timing means to time a rejectory time period extension responsive to atrial rate variability.

8. A cardiac stimulator as defined in claim 2 wherein the pulse generator includes an AV delay timer for timing an AV delay time period responsive to each conducted atrial activation and said output stage for delivering a pacing pulse to the ventricular lead responsive to the AV delay timer completing the timing of the AV delay time period.

9. A cardiac stimulator as defined in claim 8 further including an AV delay processor connected to the sensor coupled to the atrial lead and to the AV delay timer for determining the AV delay time period and providing the AV delay time period to the AV delay timer.

10. A cardiac stimulator as defined in claim 8 further including an AV delay processor connected to the sensor coupled to the atrial lead and to the AV delay timer for determining an AV delay time period responsive to each detected atrial activation and providing the AV delay time period to the AV delay timer.

11. A method for detecting atrial activations of a heart through an atrial lead associated with at least one of the atria of the heart and delivering ventricular pacing pulses to the heart through a ventricular lead associated with at least one of the ventricles of the heart, comprising the steps of:

detecting atrial activations through the atrial lead;

initiating timing of a rejectory time period responsive only to each detected atrial activation occurring outside of a rejectory time period; and delivering a ventricular pacing pulse to the heart through the ventricular lead responsive only to a detected atrial activation occurring outside of a rejectory time period.

12. A method for detecting atrial activations of a heart through an atrial lead associated with at least one of the atria of the heart and delivering ventricular pacing pulses to the heart through a ventricular lead associated with at least one of the ventricles of the heart, comprising the steps of:

detecting atrial activations through the atrial lead;

timing a rejectory time period responsive to each detected atrial activation occurring outside of a rejectory time period;

providing a conducted atrial activation responsive only to a detected atrial activation occurring outside of a rejectory time period; and delivering a pacing pulse to the ventricular lead responsive to a conducted atrial activation.

* * * * *